US008235877B2

(12) United States Patent
Boren

(10) Patent No.: US 8,235,877 B2
(45) Date of Patent: Aug. 7, 2012

(54) APPARATUS AND METHOD OF GRAVITY-ASSISTED SPINAL STRETCHING

(76) Inventor: John P. Boren, Katy, TX (US)

( * ) Notice: Subject to any disclaimer, the term of this patent is extended or adjusted under 35 U.S.C. 154(b) by 18 days.

(21) Appl. No.: 12/718,838

(22) Filed: Mar. 5, 2010

(65) Prior Publication Data

US 2011/0218086 A1 Sep. 8, 2011

(51) Int. Cl.
*A63B 26/00* (2006.01)
*A61F 5/00* (2006.01)

(52) U.S. Cl. ........................................ 482/142; 606/243

(58) Field of Classification Search .................. 482/142, 482/907, 95–96; 606/243–244
See application file for complete search history.

(56) References Cited

U.S. PATENT DOCUMENTS

| | | | | |
|---|---|---|---|---|
| 1,374,115 | A * | 4/1921 | Roemer | 606/243 |
| 1,530,519 | A | 3/1925 | Remington | |
| 1,915,841 | A * | 6/1933 | Warner | 606/243 |
| 2,828,735 | A | 4/1958 | Thompson | |
| 2,831,482 | A | 4/1958 | Cobb | |
| 3,265,065 | A | 8/1966 | Jillson | |
| 3,640,520 | A | 2/1972 | Wieland et al. | |
| 3,695,256 | A | 10/1972 | Brower | |
| 3,709,217 | A | 1/1973 | Powers | |
| 3,741,200 | A | 6/1973 | Morin | |
| 3,771,518 | A | 11/1973 | Greissing | |
| 3,814,414 | A | 6/1974 | Chapa | |
| 3,868,103 | A | 2/1975 | Pageot et al. | |
| 3,926,182 | A | 12/1975 | Stabholz | |
| 4,111,414 | A | 9/1978 | Roberts | |
| 4,149,714 | A | 4/1979 | Lambert, Jr. | |
| 4,198,044 | A | 4/1980 | Holappa | |
| 4,200,279 | A | 4/1980 | Lambert, Jr. | |
| 4,211,426 | A | 7/1980 | Motloch | |
| 4,322,071 | A | 3/1982 | Lambert, Jr. et al. | |
| 4,337,050 | A | 6/1982 | Engalitcheff, Jr. | |
| 4,372,551 | A | 2/1983 | Yurdin | |
| 4,372,552 | A | 2/1983 | Carlmark | |
| 4,372,553 | A | 2/1983 | Hatfield | |
| 4,524,763 | A | 6/1985 | Eberling, Jr. | |

(Continued)

FOREIGN PATENT DOCUMENTS

| | | |
|---|---|---|
| DE | 76054 | 11/1893 |

(Continued)

OTHER PUBLICATIONS

Loredan Biomedical, Inc. LIDO Strength Training System, Advertisement, © 1992.

(Continued)

*Primary Examiner* — Fenn Mathew
(74) *Attorney, Agent, or Firm* — Gary L. Bush; Andrews Kurth LLP

(57) ABSTRACT

An apparatus and method for stretching and/or exercising a user's body through incremental, controlled inversion and lower body stretching, preferably performed in combination. The user lies atop an exercise table and restrains her lower body to a restraint movably coupled to the exercise table. The user preferably controls the actuation of a first actuator to incrementally pivot the exercise table about a support structure thereby inverting the user's body. Before or after actuation of the first actuator, but preferably concurrently therewith, the user controls the actuation of a second actuator to incrementally extend the restraint axially away from the exercise table thereby pulling the user's lower body away from the user's upper body. This combination of gravity and mechanical decompression produces greater results than either action by itself.

13 Claims, 7 Drawing Sheets

U.S. PATENT DOCUMENTS

| | | | | | |
|---|---|---|---|---|---|
| 4,593,909 | A | | 6/1986 | Anselmo et al. | |
| 4,608,969 | A | * | 9/1986 | Hamlin | 606/243 |
| 4,628,910 | A | | 12/1986 | Krukowski | |
| 4,672,697 | A | | 6/1987 | Schurch | |
| 4,691,694 | A | | 9/1987 | Boyd et al. | |
| 4,725,056 | A | | 2/1988 | Rehrl et al. | |
| 4,768,783 | A | | 9/1988 | Engalitcheff, Jr. | |
| 4,834,365 | A | | 5/1989 | Jones | |
| 4,836,536 | A | | 6/1989 | Jones | |
| 4,845,987 | A | | 7/1989 | Kenneth | |
| 4,881,528 | A | | 11/1989 | Scott | |
| 4,890,604 | A | | 1/1990 | Nelson | |
| 4,911,106 | A | | 3/1990 | Goodwin | |
| 4,915,101 | A | * | 4/1990 | Cuccia | 606/244 |
| 4,987,622 | A | | 1/1991 | Shockey | |
| 5,020,520 | A | | 6/1991 | Lawlis | |
| 5,042,796 | A | | 8/1991 | Jibril | |
| 5,044,359 | A | * | 9/1991 | Reinert | 606/243 |
| 5,048,541 | A | | 9/1991 | Haneline | |
| 5,094,249 | A | | 3/1992 | Marras et al. | |
| 5,105,803 | A | | 4/1992 | Burton | |
| 5,129,881 | A | | 7/1992 | Pope | |
| 5,147,287 | A | | 9/1992 | Jewell et al. | |
| 5,213,556 | A | | 5/1993 | Boren | |
| 5,217,488 | A | * | 6/1993 | Wu | 606/241 |
| 5,242,347 | A | | 9/1993 | Keeton | |
| 5,263,913 | A | | 11/1993 | Boren | |
| 5,263,914 | A | | 11/1993 | Simonson et al. | |
| 5,308,359 | A | | 5/1994 | Lossing | |
| 5,324,247 | A | | 6/1994 | Lepley | |
| 5,354,251 | A | | 10/1994 | Sleamaker | |
| 5,409,452 | A | | 4/1995 | Aversano | |
| 5,474,086 | A | | 12/1995 | McCormick et al. | |
| 5,529,558 | A | | 6/1996 | Koenig | |
| 5,577,503 | A | | 11/1996 | Bonutti | |
| 5,595,192 | A | | 1/1997 | Tatum | |
| 5,688,212 | A | | 11/1997 | Walker | |
| 5,704,881 | A | | 1/1998 | Dudley | |
| 5,752,879 | A | * | 5/1998 | Berdut | 482/96 |
| 5,766,115 | A | | 6/1998 | Huang | |
| 5,860,899 | A | | 1/1999 | Rassman | |
| 5,868,691 | A | | 2/1999 | Vishnevsky | |
| 5,897,472 | A | | 4/1999 | Thulasingam | |
| 5,943,983 | A | | 8/1999 | Drew et al. | |
| 6,083,183 | A | | 7/2000 | Yang | |
| 6,146,317 | A | | 11/2000 | Prusick | |
| 6,202,230 | B1 | | 3/2001 | Borders | |
| 6,458,060 | B1 | | 10/2002 | Watterson et al. | |
| 6,551,214 | B1 | | 4/2003 | Taimela | |
| 6,656,098 | B2 | | 12/2003 | Hoffman | |
| 6,672,998 | B2 | | 1/2004 | Cook | |
| 6,689,027 | B1 | | 2/2004 | Gardikis, Jr. | |
| 6,749,548 | B2 | | 6/2004 | Hoffman | |
| 6,790,194 | B1 | | 9/2004 | Katane et al. | |
| 6,814,708 | B1 | | 11/2004 | Jennings | |
| 6,817,363 | B2 | | 11/2004 | Biondo et al. | |
| 7,070,548 | B2 | | 7/2006 | Thonn, Jr. | |
| 7,097,628 | B1 | | 8/2006 | Baune | |
| 7,125,167 | B2 | | 10/2006 | Alakkat | |
| 7,125,370 | B1 | | 10/2006 | Schaffner et al. | |
| 7,255,708 | B2 | | 8/2007 | Kim et al. | |
| 7,311,645 | B1 | | 12/2007 | Lynch et al. | |
| 7,402,128 | B2 | | 7/2008 | Thonn, Jr. | |
| 2002/0000008 | A1 | | 1/2002 | Borders | |
| 2002/0111257 | A1 | | 8/2002 | Hur | |
| 2002/0183177 | A1 | | 12/2002 | Hoffman | |
| 2003/0017925 | A1 | | 1/2003 | Hoffman | |
| 2003/0087736 | A1 | | 5/2003 | Carter et al. | |
| 2005/0181917 | A1 | | 8/2005 | Dayal | |
| 2006/0019805 | A1 | | 1/2006 | Heck | |
| 2006/0035769 | A1 | | 2/2006 | Phillips | |
| 2006/0048785 | A1 | | 3/2006 | Dalen et al. | |
| 2006/0074366 | A1 | | 4/2006 | Ryan et al. | |
| 2007/0093367 | A1 | | 4/2007 | Walton | |
| 2007/0157393 | A1 | | 7/2007 | Gerlach | |
| 2008/0176714 | A1 | | 7/2008 | Boren | |
| 2008/0176716 | A1 | | 7/2008 | Boren | |
| 2008/0176721 | A1 | | 7/2008 | Boren | |
| 2008/0177211 | A1 | | 7/2008 | Boren | |
| 2008/0269030 | A1 | | 10/2008 | Hoffman et al. | |

FOREIGN PATENT DOCUMENTS

| | | | |
|---|---|---|---|
| DE | 19852183 | A1 | 5/2000 |
| DE | 19882183 | A1 | 5/2000 |
| FR | 2502487 | A | 3/1981 |
| JP | 06054871 | | 3/1994 |
| JP | 06054871 | A | 3/1994 |

OTHER PUBLICATIONS

The ATM (Active Therapeutic Movement) Concept—A White Paper (undated).

Giammatteo, S.W., "Relevance of ATM with Neurologically Impaired Adults" BackProject Corporation, http://backproject.com/articles/articles_neuro_applicability.html.

ATM2-MD (Mini-Door-Model), BackProject Corporation http://backproject.com/products/prod_ATM2_MD.html.

* cited by examiner

APPARATUS AND METHOD OF GRAVITY-ASSISTED SPINAL STRETCHING

BACKGROUND OF THE INVENTION

1. Field of the Invention

This invention relates generally to an apparatus and method for stretching and exercising the human body. Specifically, the invention relates to a user-controlled apparatus for stretching and exercising a user's spine or torso while positioned in variable angles of inversion relative to the horizon.

2. Description of the Related Art

Numerous medical and non-medical mechanical devices are known in the art for stretching the human frame. These mechanical devices include both motorized and non-motorized movement, and employ various methods of weight resistance, plyometric resistance and/or gravity assistance to accomplish the goal of stretching, flexing, and/or unloading the human frame. Purely medical devices have included over-the-door and power-activated stretching devices, among others, arranged and designed to decompress the spine. Non-medical devices have typically included gym-type equipment including, but not limited to, gravity balls, and Pilates machines, arranged and designed to stretch the targeted muscles, improve flexibility, and increase the range of joint motion.

Among the more common types of devices for stretching the human frame are "inversion" devices, which operate by inverting the human body. These inversion devices suspend the user in an upside down position by the ankles or knees so that the spine and associated structures, which produce vertical pressure while in an upright position, may be unloaded and thereby stretched. The principle behind these inversion devices is that, by turning the human frame upside down, gravity acting on the human frame in the reverse direction will facilitate the relaxation of the spine and associated structures, thereby giving the user a sense of comfort and well being. Unfortunately, inversion devices and other fitness-oriented exercise and stretching devices have typically been uncomfortable, cumbersome, and/or difficult to operate, especially for older users. Furthermore, common place fitness-oriented exercise and stretching devices are not necessarily directed at conditioning and unloading the user's spine and/or torso section in a controlled manner.

3. Identification of Objects of the Invention

An object of the invention is to accomplish one or more of the following:

Provide an apparatus and method for stretching and/or exercising the human body, and particularly the abdominal and/or back muscles, in a controlled manner;

Provide an apparatus and method for unloading or decompressing the human spine;

Provide an apparatus and method for axially stretching the human body in a controlled and/or incremental manner;

Provide an apparatus and method for inverting the human body from a horizontal or near horizontal position in a controlled and/or incremental manner;

Provide an apparatus and method for axially stretching the human body while simultaneously inverting the human body, both in a controlled and/or incremental manner; and Provide an apparatus and method for stretching and/or exercising the human body that is controlled by the user.

Other objects, features, and advantages of the invention will be apparent to one skilled in the art from the following specification and drawings.

SUMMARY OF THE INVENTION

The objects identified above, along with other features and advantages of the invention are incorporated in an apparatus and method for stretching and/or exercising portions of the human body such as, but not limited to, the neck, the shoulders, the spine (e.g., the cervical and lumbar regions), the knees, the legs and thighs, and the muscles of the back and abdomen. The apparatus of a preferred implementation comprises a tabletop or bed carried by a support structure. A restraint, movably coupled to the tabletop, is disposed at one end of the tabletop to receive and capture a portion of the lower body of the user while the user lies either prone or supine upon the tabletop. A first actuator, controlled by the user via a handheld control device, is arranged and designed to pivot the tabletop about the support structure, thereby inverting the user's body. The user is held in position about the tabletop by the combination of the user's lower body held by the restraint and the user's own body weight. A second actuator, also controlled by the user via the handheld control device, is arranged and designed to move the restraint away from the tabletop, thereby pulling the user's lower body relative to her upper body. In a preferred implementation of the apparatus and method, the user actuates both the first and second actuators in order to simultaneously invert the tabletop and move the restraint away from the tabletop. In this way, the user's body is stretched and exercised at the same time both axially, via action of the restraint, and gravitationally, via action of the tabletop inversion. This combination of gravity and mechanical decompression produces greater therapeutic variations than performing each action independently.

BRIEF DESCRIPTION OF THE DRAWINGS

By way of illustration and not limitation, the invention is described in detail hereinafter on the basis of the accompanying figures, in which.

DESCRIPTION OF THE PREFERRED IMPLEMENTATIONS OF THE INVENTION

Figure 1:
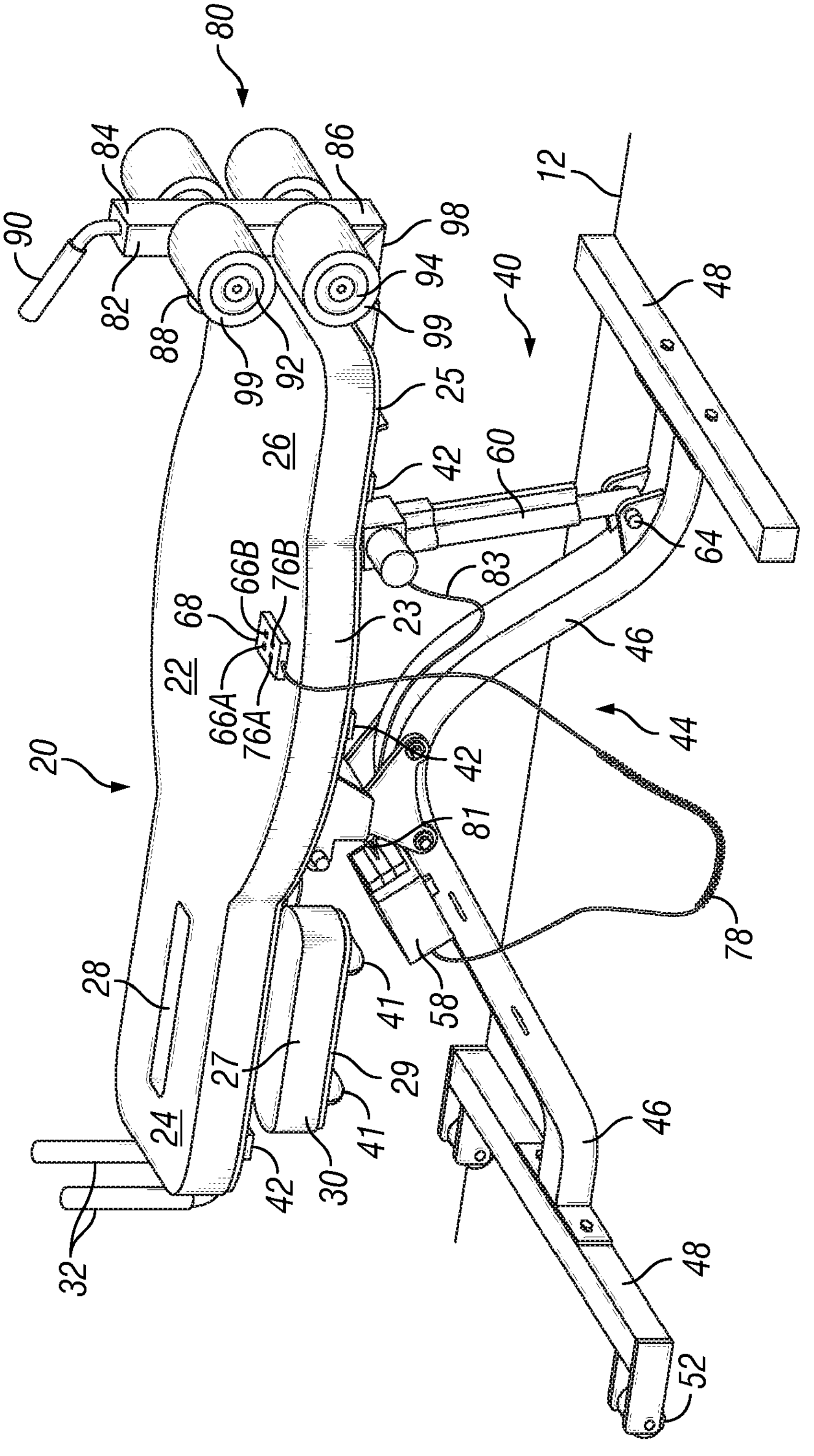
FIG. 1 is a prospective view of the apparatus according to a preferred implementation of the invention.

A preferred implementation of the invention alleviates one or more of the deficiencies of the prior art and incorporates at least one of the objects previously identified. Referring now to the drawings, FIG. 1 illustrates a preferred implementation of the invention comprising an apparatus (i.e., exercise machine) 10 arranged and designed to stretch and/or exercise the human body, including the abdominal and/or back muscles, in a controlled manner. The exercise machine 10 comprises a table 20 having a tabletop 22 carried by a support structure 40. The tabletop 22 has an upper section 24 that receives a user's upper body, and a lower section 26 that receives a user's lower body, when the user lies horizontally thereon. The upper section 24 of the tabletop 22 preferably has an aperture 28 therein which receives the user's face when the user is lying in a prone position on the tabletop 22. While the aperture 28 shown in FIG. 1 has a slot shape that accommodates a user's face regardless of the user's body length (i.e., height) when lying prone on the table 20, the optional aperture 28 may have any desired shape. The tabletop 22 preferably includes a pad 23 or other type of cushion positioned overtop of an underlying layer 25 having a more rigid structure, such as that provided by a wood board or a metal plate/mesh. The tabletop 22 also includes a frame 42 having a plurality of members which are coupled to and carry the underlying layer 25. Thus, as used herein, tabletop 22 refers to the structure 23, 25, 42 carried by support structure 40.

As shown in FIG. 1, one or more vertical handles 32 are also preferably coupled to the tabletop 22 (e.g., by bolting or welding the handles 32 to the frame 42) near an upper section 24 of the tabletop 22. These handles 32 permit the user to firmly hold onto the table 20 while assuming a horizontal position atop the table 20, exiting the table 20, or when performing one or more of the exercises using the machine 10. As used herein, coupling may be accomplished in any known manner to those of skill in the art to join or link two things together. As further illustrated in FIG. 1, two arm rests 30 are adjustably coupled to the tabletop 22 such that an arm rest 30 is positioned on each side of the table 20 towards the upper section 24 of the tabletop 22. The arm rests 30 may be permanently positioned at a vertical height that is the same as, higher than, or lower than the adjacent tabletop 22. Preferably, however, the vertical heights of the arm rests 30 are independently adjustable with respect to the adjacent tabletop 22. Similar to tabletop 22, the arm rests 30 are constructed of a padded layer 27 and a rigid layer 29 and are supported by a frame 41, which is adjustably coupled to frame 42 of tabletop 22.

Figure 2:
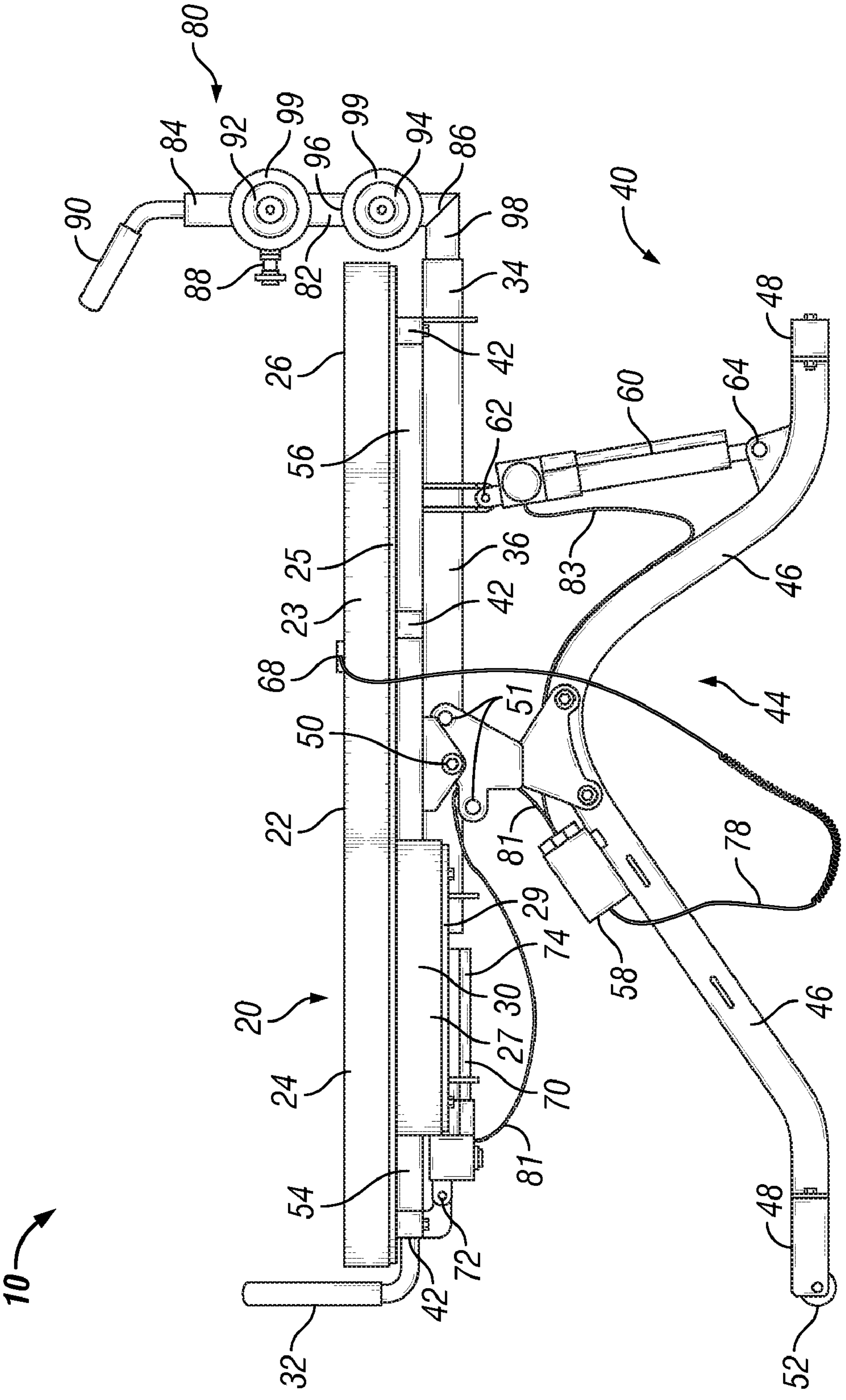
FIG. 2 is a side view of the apparatus of FIG. 1.
Figure 3:
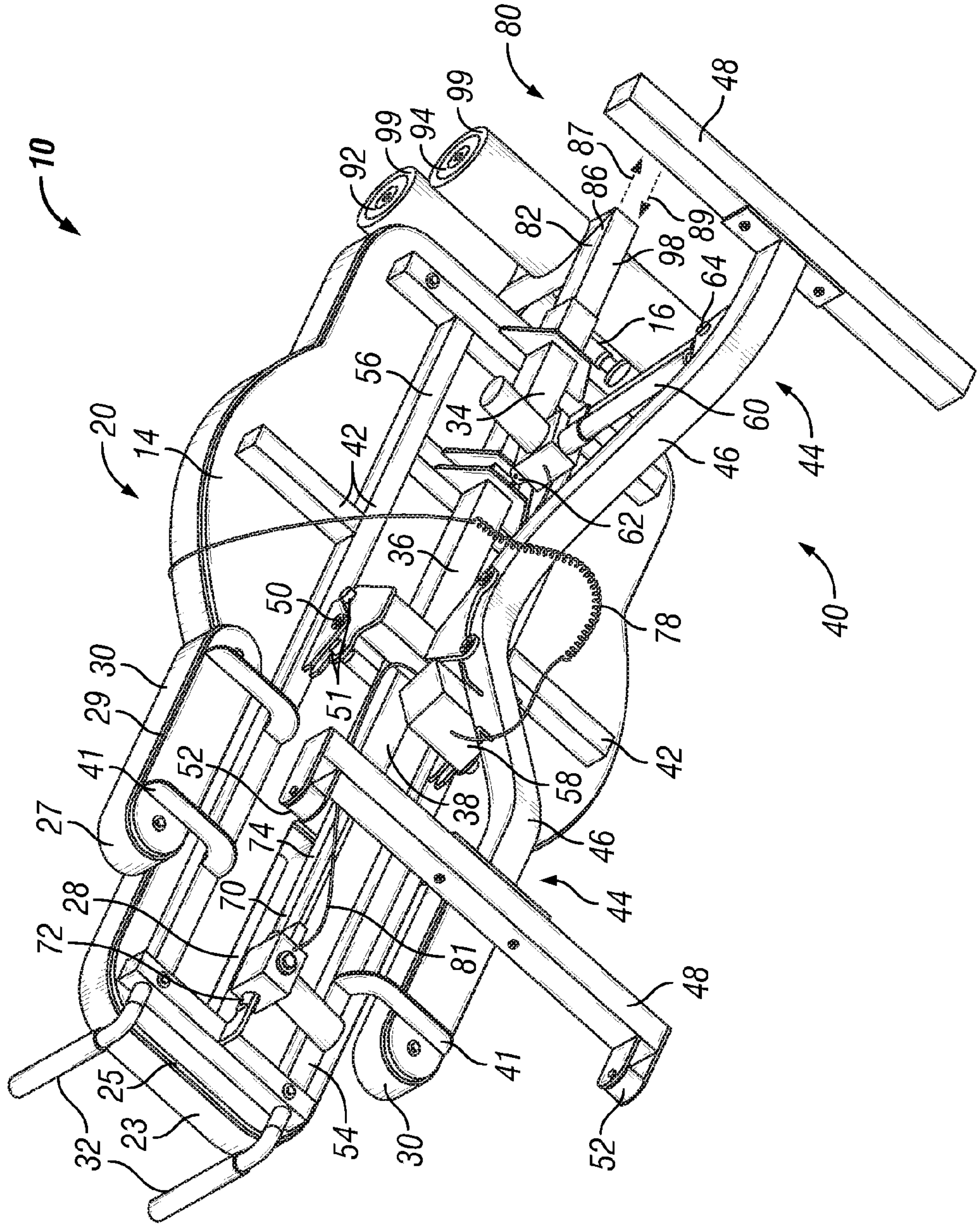
FIG. 3 is a bottom or underside view of the apparatus of FIG. 1.

The support structure 40 is comprised of a vertical support 44, which elevates the tabletop 22 above ground level 12. As shown in FIG. 1, frame 42 of tabletop 22 is carried by a vertical support 44 comprising two legs 46. Each leg 46 has a perpendicular base 48 which stabilizes the two legs 46 about the floor or ground 12 in a vertical or near vertical position. A plurality of rollers 52 are preferably disposed on the underside of at least one of the perpendicular bases 48 to permit easy movement of the table 20 from one location to another. While the vertical support 44 shown in FIG. 1 is preferred, other structures, i.e., a pedestal, more than two legs, a solid base, etc, that serve the same function, i.e., supporting the tabletop 22 above ground level 12, are well known in the art and may alternatively be employed. As is best shown in FIGS. 2 and 3, frame 42 is movably coupled to the vertical support 44 through a coupler 50, which is arranged and designed to permit frame 42 and hence tabletop 22 to pivot about the vertical support 44 at the coupler 50. The coupler 50 shown in FIG. 2 includes a nut and bolt combination that permits frame 42 and the vertical support 44 to pivot relative to each other at the joint between the two members 42, 44. Alternative types of couplers, e.g., pins, that permit a pivoting action are well known to those of skill in the art and may be equally used. The vertical support 44 and/or the frame 42 may be arranged and designed to permit frame 42 to pivot in only one direction and/or only within a narrow range (i.e., between stops 51 as best shown in FIG. 2) relative to the vertical support 44.

As shown in FIG. 2, a first actuator 60 is preferably movably coupled between the frame 42 and the vertical support 44 such that one end portion 62 is movably coupled to the lower section 56 of frame 42 (i.e., beneath the lower section 26 of the tabletop 22) and the other end portion 64 is movably coupled to the vertical support 44. The first actuator 60 may be electrically, mechanically, hydraulically, or pneumatically operated and is preferably controlled by the user via a control module 58 positioned on the vertical support 44 as shown in FIGS. 1 and 2. While the first actuator 60 is preferably an electric actuator, it may be any linearly-acting actuator known in the art for extending from and retracting to an original starting position, preferably in an incremental manner. Activation or extension of the first actuator 60 to its fully actuated or extended position, or any position therebetween, raises the lower section 56 of frame 42 (i.e., lower section 26 of tabletop 22), thereby pivoting the frame 42 (i.e., tabletop 22) about the vertical support 44 at coupler 50. Pivoting frame 42 and hence tabletop 22 causes the upper section 54 of frame 42 (i.e., upper section 24 of tabletop 22) to be lowered relative to ground level 12 and the lower section 56 of frame 42 (i.e., lower section 26 of tabletop 22) to be raised relative to ground level 12. A previously activated or extended first actuator 60 may be retracted to its original starting position, or any position therebetween, thereby pivoting frame 42 (i.e., tabletop 22) about the vertical support 44 at the coupler 50 in the opposite direction. Returning the first actuator 60 to its original starting position returns the frame 42 of tabletop 22 to a horizontal or near horizontal position.

As best shown in FIGS. 2 and 3, a rigid foot restraint assembly 80, positioned perpendicularly to frame 42, is movably coupled to the lower section 56 of frame 42. The rigid foot restraint assembly 80 acts as an ankle support or brace and is preferably comprised of a vertical member 82 having a vertically adjustable portion 84 and a fixed portion 86. The vertically adjustable portion 84 is arranged and designed to be releasably fastened to the fixed portion 86 through restraint catch 88 but to slide vertically within the fixed portion 86 when restraint catch 88 is released. The vertically adjustable portion 84 and the fixed portion 86 of the vertical member 82 each have a horizontal bar or member 92, 94 coupled thereto in opposing fashion, as best shown in FIG. 1. The upper 92 and lower 94 horizontal members are shown with cushions 99 disposed thereon for the comfort of the user.

Release of restraint catch 88 from engagement with vertical member 82 permits vertically adjustable portion 84, and thus upper horizontal member 92, to move vertically relative to lower horizontal member 94 of fixed portion 86. Vertical movement of the upper horizontal member 92 is achieved by the user pulling up or pushing down on the vertically adjustable portion 84 of the vertical member 82, preferably by the handle 90 attached thereto. Handle 90 may also be used by the user to facilitate entering or leaving a position atop the tabletop 22. Alternatively, vertical movement of the upper horizontal member 92 may be achieved mechanically via an actuator (not shown), preferably controlled by the user. After the desired vertical position of the upper horizontal member 92 relative to the lower horizontal member 94 is achieved, the restraint catch 88 is reengaged with vertical member 82 thereby fastening the vertically adjustable portion 84 to fixed portion 86. As best shown in FIG. 2, the top 96 of the lower horizontal member 94 is preferably at the same vertical level as the tabletop 22, thereby forming an artificial horizontal extension thereof. Nevertheless, the vertical height of the lower horizontal member 94 coupled to the fixed portion 86 of the vertical member 82 could be adjusted and fixed in any manner known to those of skill in the art.

FIG. 3 illustrates the underside 14 of the exercise machine 10 of FIGS. 1 and 2. As shown, vertical member 82 of rigid restraint 80 has a horizontal portion 98 coupled to its fixed portion 86, which is adjustably coupled via underside catch 16 to one end portion 34 of a longitudinal member or carrier shaft 36 that axially traverses the underside of tabletop 22. Underside catch 16 operates similarly to the restraint catch 88 described above. Thus, the horizontal portion 98 of vertical member 82 is arranged and designed to be releasably fastened to the longitudinal member 36 through underside catch 16 when engaged but to slide horizontally within the longitudinal member 36 when the underside catch 16 is released. In this way, the position of the vertical member 82 relative to the lower section 26 of the tabletop 22 may be manually adjusted, for example, to account for user height differences.

As shown in FIG. 3, a second actuator 70 is coupled between frame 42 of tabletop 22 and the longitudinal member 36 such that one end portion 72 of the second actuator 70 is coupled to the upper section 54 of frame 42 (i.e., the upper section 24 of the tabletop 22) and the other end portion 74 is coupled to the other end portion 38 of longitudinal member 36. The second actuator 70 may be electrically, mechanically, hydraulically, or pneumatically operated and is preferably controlled by the user via the control module 58 positioned on the vertical support 44. While the second actuator 70 is preferably an electric actuator, it may be any linearly-acting actuator known in the art for extending from and retracting to an original starting position, preferably in an incremental manner. Activation or extension of the second actuator 70 to its fully activated or extended position, or any position therebetween, extends the vertical member 82 (i.e., restraint 80) axially, or longitudinally, away from the lower section 26 of the tabletop 22 (i.e., in the direction of arrow 87). A previously activated or extended second actuator 70 may be retracted to its original starting position, or any position therebetween, thereby moving the vertical member 82 in the opposite direction (i.e., towards the lower section 26 of the tabletop 22 as shown by the direction of arrow 89). As described above, the starting position of the vertical member 82 relative to the lower section 26 of the tabletop 22 may be adjusted via the underside catch 16.

Returning to FIG. 1, a handheld control device 68, which may be user-operated while using the exercise machine 10, is shown for controlling the movement of the first 60 and second 70 actuators. The handheld control device 68 has a first actuator switch or one or more buttons 66A, 66B (i.e., inversion buttons) that send a signal to actuate or de-actuate the first actuator 60 and a second actuator switch or one or more buttons 76A, 76B (i.e., axial buttons) that send a signal to actuate or de-actuate the second actuator 70. As shown, the handheld control device 68 has two inversion buttons 66A, 66B, such that a first inversion button 66A actuates the first actuator 60 and a second inversion button 66B de-actuates the first actuator 60, as well as two axial buttons 76A, 76B, such that a first axial button 76A actuates the second actuator 70 and a second axial button 76B de-actuates the second actuator 70. The inversion 66A, 66B and axial 76A, 76B buttons are arranged and designed so that when a button is pressed, the respective button either actuates or de-actuates the first 60 or second 70 actuator, but when none of the buttons are pressed, the first 60 and second 70 actuators maintain their current position or state of actuation. Those skilled in the art will readily recognize that controlling the actuation/deactuation of first 60 and second 70 actuators may be achieved in other known ways, such as via switches, dials, fewer buttons, etc. The user may secure the handheld control device 68 to her wrist using an optional wrist strap 67 (see FIGS. 4-7), which helps to prevent the handheld control device from becoming separated from the user while the user is positioned atop tabletop 22 and using the exercise machine 10.

The handheld control device 68 is preferably electrically coupled to the control module 58 through a wired link 78. However, as is well known to those skilled in the art, the handheld control device 68 may wirelessly communicate with the control module 58. The control module 58 is electrically coupled to the first 60 and second 70 actuators, e.g. through wired links 83, 81, in order to control and power the actuation and de-actuation of the first 60 and second 70 actuators as commanded via the handheld control device 68. While not shown, the control module 58 may also be arranged to wirelessly communicate with the first 60 and second 70 actuators, which would be independently powered. Alternatively, the handheld control device 68 may directly control (not shown) one or both of the first 60 and second 70 actuators without the use of a centrally-located control module 58. A battery back-up system (not shown) is preferably electrically coupled to the first 60 and/or second 70 actuators so that the user may return the exercise machine 10 to a horizontal position if electrical power to the actuators 60, 70 is interrupted for any reason.

Figure 4:
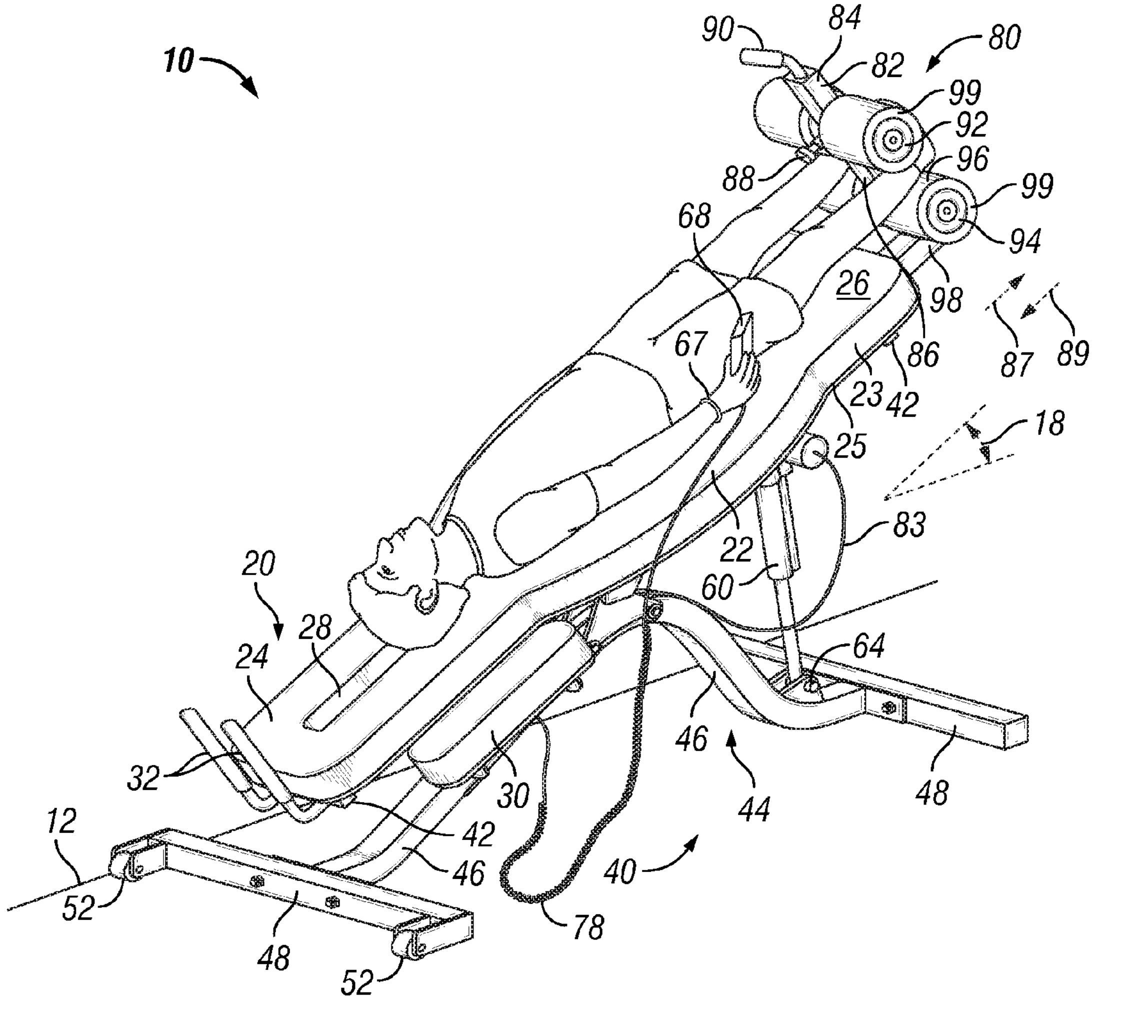
FIG. 4 is an illustration of the apparatus of FIG. 1 showing the apparatus in use by a user lying in a supine position thereon.
Figure 5:
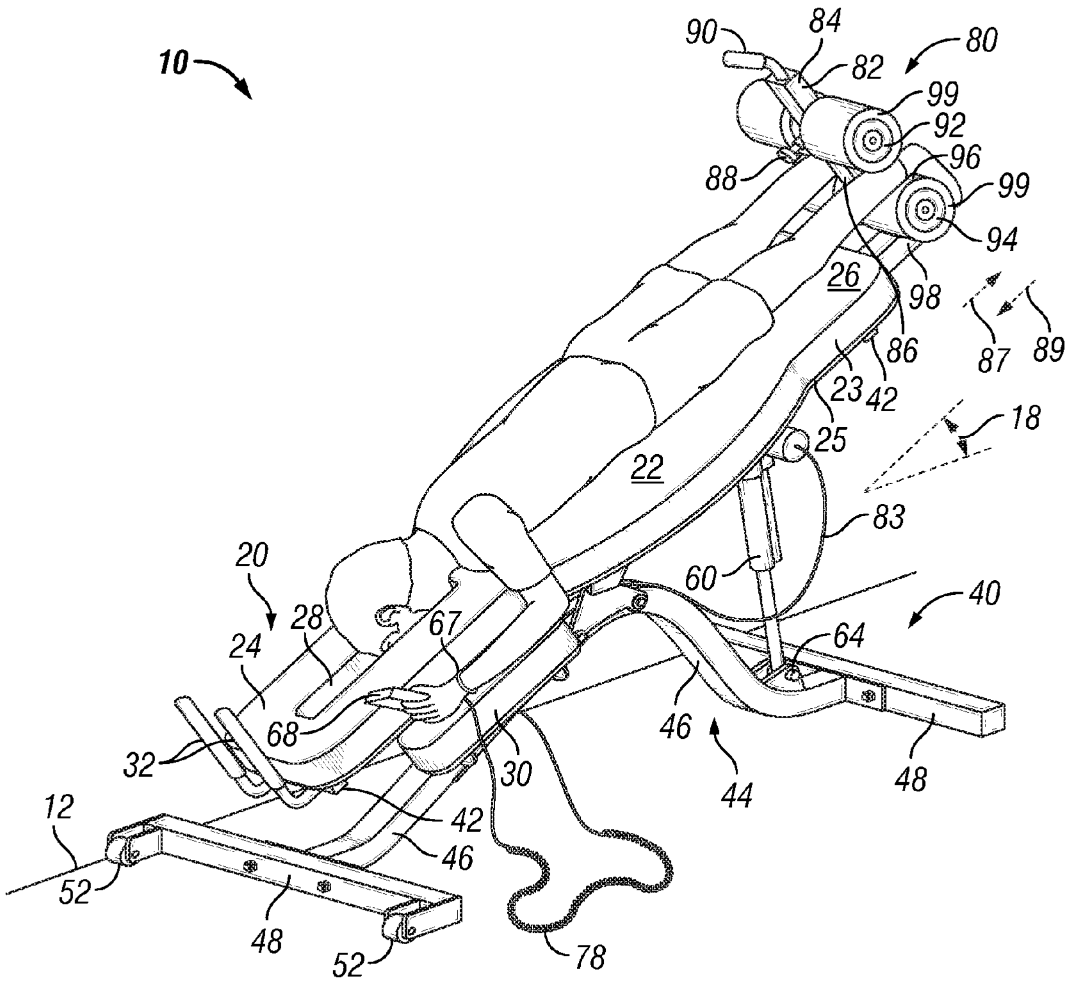
FIG. 5 is an illustration of the apparatus of FIG. 4 showing the apparatus in use by a user lying in a prone position thereon.

In a preferred method of using the apparatus (i.e., exercise machine) 10, as generally shown in FIGS. 4 and 5, the user positions herself on top of the tabletop 22 in either a supine (see FIGS. 4, 6 and 7) or prone (see FIG. 5) position. After the user places her lower legs between upper 92 and lower 94 horizontal members of rigid foot restraint assembly 80 such that her lower legs rest on top 96 of the lower horizontal member 94, the upper horizontal member 92 may be moved toward the lower horizontal member 94, as described above, thereby restraining and/or locking the user's ankles and feet (i.e., a lower portion of the user's body) between the upper 92 and lower 94 horizontal members. After the user has initially fixed the position of the upper horizontal member 92 relative to the lower horizontal member 94, the user may thereafter restrain her body by sliding her left leg in between the upper 92 and lower 94 horizontal members from the opening on the left side and her right leg in between the upper 92 and lower 94 horizontal members from the opening on the right side. The user may become unrestrained by sliding her legs out from in between the upper 92 and lower 94 horizontal members via the open sides.

Once restrained atop the exercise machine 10, the user controls the actuation/de-actuation of first 60 and second 70 actuators using the handheld control device 68. The user or an attendant controls the actuation of the first actuator 60 by pressing first inversion button 66A (FIG. 1) to raise the lower section 26 of the tabletop 22, pivot the tabletop 22 about vertical support 44 at coupler 50, and lower the upper section 24 of the tabletop 22, as shown actuated in FIGS. 4 and 5. After the user stops pressing first inversion button 66A, the actuation of the first actuator 60 ceases and the first actuator 60 remains in its then current position. In this way, the user may incrementally increase the angle of inversion 18, and thus the degree to which her body is inverted, while lying supine or prone on top of the tabletop 22. The user or attendant controls the de-actuation of the first actuator 60 by pressing second inversion button 66B (FIG. 1) to pivot the tabletop 22 in the opposition direction, thereby decreasing the angle of inversion 18. After the user stops pressing second inversion button 66B, the de-actuation of the first actuator 60 ceases and the first actuator 60 remains in its then current position.

When the tabletop 22 moves from a horizontal state to an inverted state, the user remains atop the tabletop 22 via the user's lower body, which is trapped by the user's ankles/feet between the upper 92 and lower 94 horizontal members of the rigid foot restraint assembly 80. The user's own body weight also assists in keeping the user in contact with the tabletop 22 while the tabletop 22 is in various angles of inversion 18. The user-controlled inversion of the tabletop 22 effectively stretches and exercises the user's body via gravity. Furthermore, the amount and duration of any actuation/de-actuation of first actuator 60 is controlled by the user or attendant via handheld control device 68; therefore, the angle of inversion 18 of tabletop 22 may be increased or decreased, preferably in an incremental manner, in order to slowly and methodically stretch and exercise the user's body. Preferably, the angle of inversion 18 is limited to between zero and fifty degrees, more preferably to between zero and forty degrees, and most preferably to between zero and thirty degrees.

The user also controls the actuation of the second actuator 70 by pressing first axial button 76A (FIG. 1) to extend the rigid foot restraint assembly 80 axially, or longitudinally, away from the tabletop 22 (i.e., in the direction of arrow 87), for as long as first axial button 76A remains pressed or until the second actuator 70 reaches its maximum actuation or extension. Thus, the user's ankles and feet are pulled outwardly away from the rest of the user's body as the second actuator 70 axially/longitudinally moves the rigid foot restraint assembly 80. To relax the stretching, the user controls the de-actuation of the second actuator 70 by pressing second axial button 76B (FIG. 1) to retract the rigid foot restraint assembly 80 axially, or longitudinally, toward the tabletop 22 (i.e., in the direction of arrow 89), for as long as second axial button 76B remains pressed or until the second actuator 70 reaches its original starting position.

While a portion of the user's lower body is trapped between the upper 92 and lower 94 horizontal members of the rigid foot restraint assembly 80 and is subject to movement with the actuation of the rigid foot restraint assembly 80 via the second actuator 70, the user's upper body remains stationary or nearly stationary atop the tabletop 22 due to the user's own body weight. Thus, the user-controlled movement of the rigid foot restraint assembly 80 effectively stretches and exercises the user's body by pulling the user's lower body away from the user's upper body. Furthermore, the amount and duration of any actuation/de-actuation of second actuator 70 is controlled by the user or an attendant via handheld control device 68; therefore, the rigid foot restraint assembly 80 may be moved away from tabletop 22 or toward tabletop 22, preferably in an incremental manner, in order to slowly and methodically stretch and exercise the user's body.

In a preferred method, the user actuates the second actuator 70 to move the rigid foot restraint assembly 80 prior to actuating the first actuator 60 to invert the tabletop 22. This permits the user's body to be at least partially stretched prior to inversion. Alternatively, the second actuator 70 may be actuated for the first time after the tabletop 22 has been at least partially inverted by the actuation of the first actuator 60. More preferably, however, the first 60 and second 70 actuators are actuated concurrently or simultaneously, at least for a short period of time, such that the tabletop 22 is inverted while the rigid foot restraint assembly 80 is extended axially away from the tabletop 22. The simultaneous actuation of the first 60 and second 70 actuators permits the user to experience an optimal amount of stretching and exercise with minimal actuator 60, 70 movement. The user preferably actuates first actuator 60 to invert tabletop 22 and second actuator 70 to axially move restraint 80 until the angle of inversion 18 of tabletop 22 and the axial position of restraint 80 relative to tabletop 22 provide the user with a comfortable positioning. The user may then continue to actuate/de-actuate the first 60 and second 70 actuators, at user discretion, to gravitationally and/or mechanically stretch/relax her body. In an alternative method, the user may actuate first actuator 60 and then actuate second actuator 70, or vice versa, with each actuation being conducted in an incremental manner until a comfortable positioning is achieved. Again, the user may then continue to actuate/de-actuate the first 60 and second 70 actuators, at user discretion, to gravitationally and/or mechanically stretch/relax her body. Using the above methods, the combination of gravity forces acting on the user's body through inversion of the tabletop 22 and mechanical forces pulling a portion of the user's lower body away from her upper body has been found to produce greater therapeutic variations than performing each actuator movement independently from the other.

Figure 6:
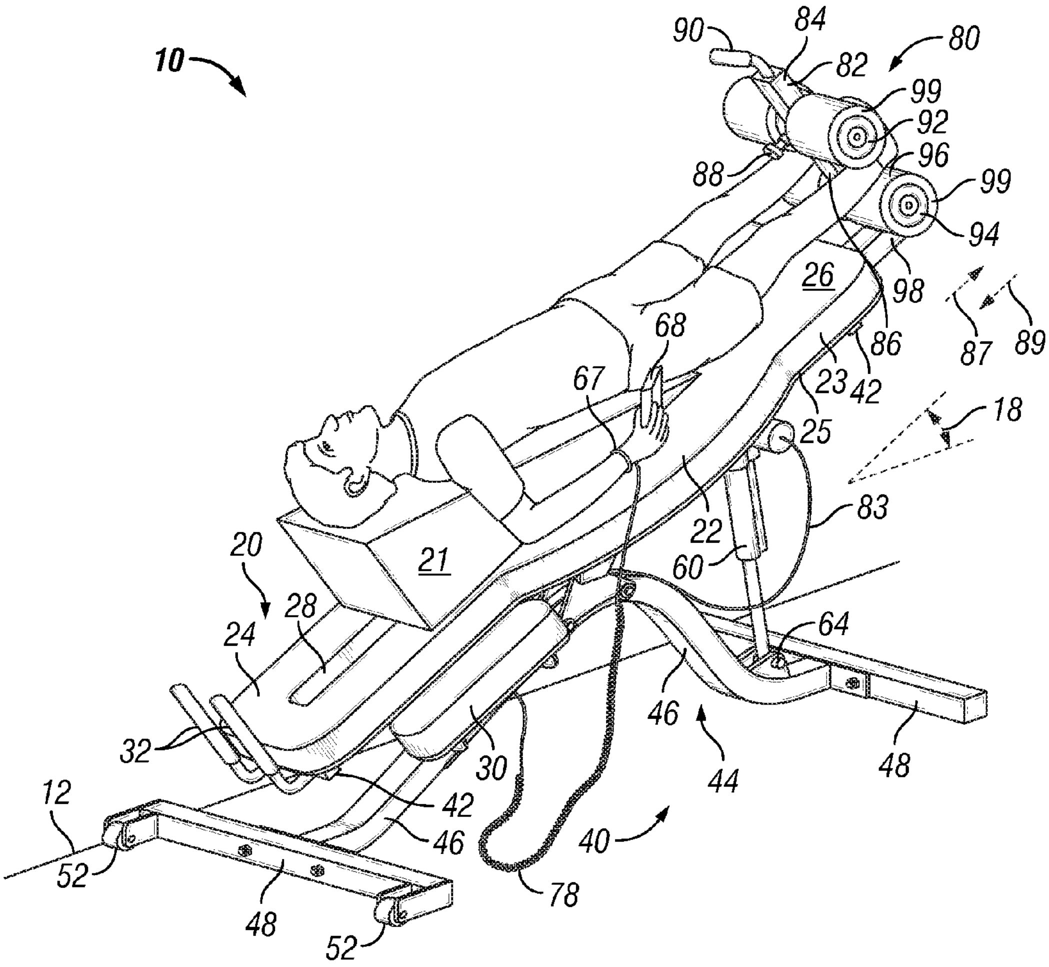
FIG. 6 is an illustration, according to an alternative implementation of the invention, of the apparatus shown in FIG. 4 in use by a user lying in a supine position thereon with a wedge-shaped cushion positioned underneath the user's upper body to maintain the user's upper body horizontal or nearly horizontal during inversion.

As shown in FIG. 6, an alternative preferred implementation of the invention employs a wedge-shaped cushion 21 positioned beneath the user's upper body to raise the user's upper body a distance above the tabletop 22. Using the wedge-shaped cushion 21 to raise the user's upper body permits the user's upper body to be maintained in a horizontal or nearly horizontal position when the user's lower body becomes inverted. The wedge-shaped cushion 21 may be dimensionally sized to raise the user's upper body any reasonable distance above the tabletop 22. Preferably, a plurality of differently-sized cushions 21 are made available to be selectively used such that the user's upper body may be maintained in a horizontal or nearly horizontal position at whatever angle of inversion 18 is desired by the user. The wedge-shaped cushion 21 may be secured to the tabletop 22 in any known manner to those skilled in the art. Preferably, a hook and loop fastener is used to releasably fasten the wedge-shaped cushion 21 to the tabletop 22, such that the cushion 21 may be easily positioned and/or repositioned beneath users of varying body lengths (i.e., heights). Additionally, the wedge-shaped cushion 21 may contoured to the user's upper body for comfort. The cushion 21 is preferably constructed of a foam material, however, any suitable material of construction known to those skilled in the art may be used. A vibrator (not shown) may be disposed within the wedge-shaped cushion 21 to provide vibration to the user's upper body while using the exercise machine 10.

Figure 7:
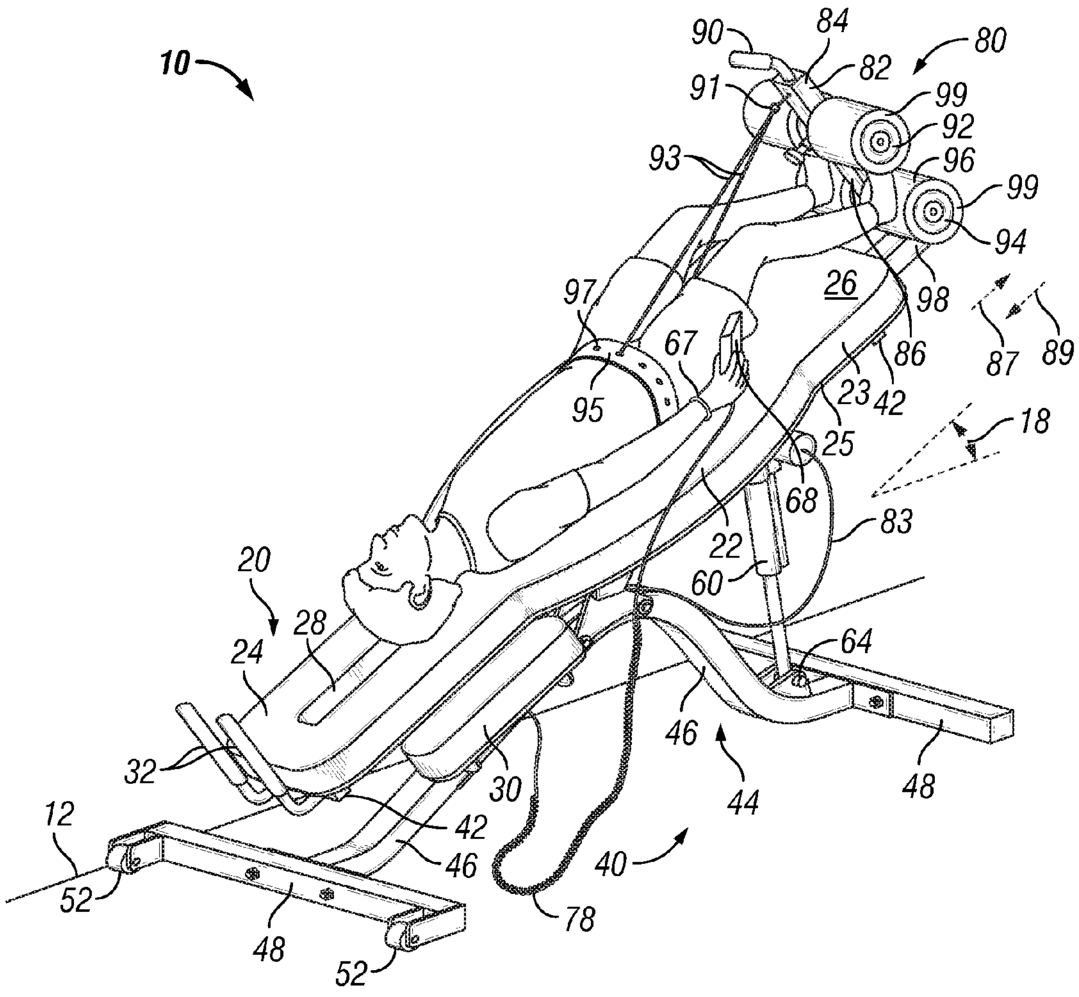
FIG. 7 is an illustration, according to an alternative implementation of the invention, in which a harness disposed about the user's lower body is coupled via a coupling to the axially movable vertical member of the movable restraint.

As shown in FIG. 7, another alternative preferred implementation of the invention employs a coupling 93 to restrain the user's lower body to the rigid foot restraint assembly 80. Coupling 93 is preferably linked between the vertically adjustable portion 84 of the vertical member 82 (i.e., rigid foot restraint assembly 80) and a belt or harness 95 disposed about the user's lower body, e.g., the user's waist. While shown as a line in FIG. 7, coupling 93 may be any type of device known to those skilled in the art for coupling one object to another including, but not limited to, a line, link, strap, rope, chain, cable, or bar. The vertically adjustable portion 80 of vertical member 82 (i.e., rigid foot restraint assembly 80) has one or more devices 91, such as hooks, eyelets, or similar devices, disposed thereon for linking coupling 93 and vertically adjustable portion 80. Harness 95 similarly has one or more devices 97, such as hooks, eyelets, or similar devices, disposed thereon for linking coupling 93 and harness 95. As shown in FIG. 7, coupling 93 is preferably coupled to a front portion of the belt or harness 95 via device 97, passed through the device 91, and coupled to a back portion (not shown) of the belt or harness 95. Alternatively, one end portion of coupling 93 may be coupled to device 91 and the other end portion of coupling 93 may be coupled to device 97 disposed on belt or harness 95. While various devices and methods for securing a user's lower body to restraint 80 are described herein, those skilled in the art will recognize that other known devices/methods may be equally employed for this purpose.

A preferred method of using the apparatus 10 shown in FIG. 7 begins with the user disposing harness 95 about her lower body, e.g., pelvis or waist. The user climbs atop table 20 and couples the coupling 93 to device 97 of harness 95 with coupling 93 passing through (or coupling to) device 91 of vertical member 82. The user disposes her legs between the upper 92 and lower 94 horizontal members of rigid foot restraint assembly 80 such that her legs rest on top 96 of the lower horizontal member 94, as previously described. Alternatively, and as shown in FIG. 7, the user may dispose her feet on the top 96 of the lower horizontal member 94 such that her knees are slightly bent. Using the rigid foot restraint assembly 80 in this way, to brace the feet between the upper 92 and lower 94 horizontal members and hold the legs elevated with the knees slightly bent, reduces the pressure of the lordotic curve. Once restrained atop the exercise machine 10, the user then controls the actuation of first 60 and second 70 actuators to stretch/exercise her body as previously described. It should be noted that operation of the second actuator 70 to move the rigid foot restraint assembly 80 axially, or longitudinally, away from tabletop 22 draws the coupling 93 taut between the rigid foot restraint assembly 80 and the harness 95 worn by the user. Continued movement of the rigid foot restraint assembly 80 away from the tabletop 22 pulls the user's lower body away from the rest of the user's body. Thus, mechanical stretching and/or exercising of the user's body is accomplished via the harness 95 and coupling 93 linked between the user's lower body and the rigid foot restraint assembly 80 and not via the user's ankles and/or feet restrained to the rigid foot restraint assembly 80. This alternative implementation may be particularly suitable to those users who suffer from pain in the legs and feet or another malady that could be exacerbated by stretching those appendages.

The Abstract of the disclosure is written solely for providing the United States Patent and Trademark Office and the public at large with a means by which to determine quickly from a cursory inspection the nature and gist of the technical disclosure, and it represents one preferred implementation and is not indicative of the nature of the invention as a whole.

While some implementations of the invention have been illustrated in detail, the invention is not limited to the implementations shown; modifications and adaptations of the disclosed implementations may occur to those skilled in the art. Such modifications and adaptations are in the spirit and scope of the invention as set forth in the claims:

What is claimed is:

1. An apparatus (10) for exercising a user's body comprising, a table (20) having a tabletop (22) and a support structure (40) elevating said tabletop above ground level (12), said tabletop having an upper section (24) to receive an upper portion of said user's body thereon and a lower section (26) to receive a lower portion of said user's body thereon, said tabletop movably coupled to said support structure;

a first actuator (60) coupled to said lower section of said tabletop, said first actuator arranged and designed to raise said lower section of said tabletop relative to ground level, thereby pivoting said tabletop relative to said support structure and lowering said upper section of said tabletop relative to ground level;

a restraint (80) movably coupled to said lower section of said tabletop, said restraint arranged and designed to restrain said user's body to said restraint;

a second actuator (70) coupled to said restraint, said second actuator arranged and designed to axially move said restraint relative to said lower section of said tabletop and to operate concurrently with said first actuator; and a control device (68) arranged and designed to control said first and second actuators (60, 70), and capable of use by said user while said user is restrained, thereby allowing said user to use said apparatus (10) without assistance from another person.

2. The apparatus of claim 1 further comprising, a cushion (21) positioned on said upper section of said tabletop, said cushion arranged and designed to receive said upper portion of said user's body thereon and to elevate said upper portion of said user's body above said upper section of said tabletop.

3. The apparatus of claim 1 further comprising, an arm rest (30) coupled to said tabletop.

4. The apparatus of claim 1 wherein, said tabletop has an aperture (28) therein arranged and designed to receive a user's face while a user lies in a prone position atop said tabletop.

5. The apparatus of claim 1 wherein, said restraint has a vertical member (82) with a lower horizontal member (94) and an upper horizontal member (92) coupled thereto, said upper and lower horizontal members arranged and designed to restrain another lower portion of said user's body therebetween.

6. The apparatus of claim 1 further comprising, a coupling (93) linked between said restraint and a harness (95) disposed about said user's body, whereby when said second actuator moves said restraint away from said tabletop, said coupling is drawn taut between said restraint and said harness.

7. An apparatus (10) for stretching a user's body comprising, a table (20) having a tabletop (22) and a support structure (40), said tabletop having an upper section (24) to receive an upper portion of said user's body thereon and a lower section (26) to receive a lower portion of said user's body thereon, said support structure arranged and designed to elevate said tabletop above ground level (12), said tabletop movably coupled to said support structure such that said tabletop pivots about said support structure;

a first actuator (60) coupled to said tabletop, said first actuator arranged and designed to raise said lower section of said tabletop relative to ground level, thereby pivoting said table top relative to said support structure and lowering said upper section of said tabletop relative to ground level;

a rigid restraint (80) movably coupled to said lower section of said tabletop, said rigid restraint arranged and designed to restrain said lower portion of said user's body to said rigid restraint;

a second actuator (70) coupled to said rigid restraint, said second actuator arranged and designed to axially move said rigid restraint relative to said lower section of said tabletop, whereby, when said user's body is disposed on said tabletop and restrained by said rigid restraint, said second actuator is actuated after said first actuator is actuated; and a control device (68) arranged and designed to control said first and second actuators (60, 70), and capable of use by said user while said user is restrained, thereby allowing said user to use said apparatus (10) without assistance from another person.

8. The apparatus of claim 7 further comprising, a cushion (21) positioned on said upper section of said tabletop, said cushion arranged and designed to receive said upper portion of said user's body thereon and to elevate said upper portion of said user's body above said upper section of said tabletop.

9. The apparatus of claim 7 further comprising, an aim rest (30) coupled to said tabletop.

10. The apparatus of claim 7 wherein, said tabletop has an aperture (28) therein arranged and designed to receive a user's face while a user lies in a prone position atop said tabletop.

11. The apparatus of claim 7 wherein, said rigid restraint has a vertical member (82) with a lower horizontal member (94) and an upper horizontal member (92) coupled thereto, said upper and lower horizontal members arranged and designed to restrain another lower portion of said user's body therebetween.

12. The apparatus of claim 7 further comprising, a coupling (93) linked between said rigid restraint and a harness (95) disposed about said user's body, whereby when said second actuator moves said restraint away from said tabletop, said coupling is drawn taut between said rigid restraint and said harness.

13. The apparatus of claim 7 wherein, said first actuator and said second actuator are arranged and designed to be actuated concurrently.

* * * * *